US011058528B2

United States Patent
Kim (10) Patent No.: US 11,058,528 B2
(45) Date of Patent: Jul. 13, 2021

(54) URINARY INCONTINENCE PREVENTION CLIP FOR MEN

(71) Applicant: Myung Sook Kim, Seoul (KR)

(72) Inventor: Myung Sook Kim, Seoul (KR)

( * ) Notice: Subject to any disclaimer, the term of this patent is extended or adjusted under 35 U.S.C. 154(b) by 239 days.

(21) Appl. No.: 16/099,184

(22) PCT Filed: Jun. 15, 2016

(86) PCT No.: PCT/KR2016/006362
§ 371 (c)(1),
(2) Date: Nov. 5, 2018

(87) PCT Pub. No.: WO2017/204397
PCT Pub. Date: Nov. 30, 2017

(65) Prior Publication Data
US 2019/0133739 A1    May 9, 2019

(30) Foreign Application Priority Data
May 23, 2016    (KR) .................. 10-2016-0062661

(51) Int. Cl.
*A61F 2/00* (2006.01)
*A61B 17/122* (2006.01)
*A61B 17/12* (2006.01)

(52) U.S. Cl.
CPC .............. *A61F 2/0054* (2013.01); *A61F 2/00* (2013.01); *A61F 2/0004* (2013.01);
(Continued)

(58) Field of Classification Search
CPC .... A61F 2/0004; A61F 2/0031; A61F 2/0054; A61B 17/12; A61B 17/122;
(Continued)

(56) References Cited

U.S. PATENT DOCUMENTS

| 3,203,421 A | 8/1965 | Bialick |
| 4,139,007 A | 2/1979 | Diamond |

(Continued)

FOREIGN PATENT DOCUMENTS

| JP | 08-008780 Y | 6/1933 |
| JP | 55-070111 U | 5/1980 |

(Continued)

OTHER PUBLICATIONS

The extended European Search Report of 16903245.5 dated Jan. 17, 2020.

(Continued)

*Primary Examiner* — Keri J Nelson
(74) *Attorney, Agent, or Firm* — Revolution IP, PLLC (57) ABSTRACT

A urinary incontinence prevention clip for men includes: a clip body having an upper frame positioned so as to correspond to the upper part of male genitalia, a lower frame positioned so as to correspond to the lower part of the male genitalia, and a connection part connected to one side of the upper frame and the lower frame and providing elastic force in a direction, in which the upper frame and the lower frame are spread; cushion parts respectively provided on the inside of the upper frame and the inside of the lower frame; and locking parts formed at both ends of the clip body so as to be fastened to each other, wherein the upper frame is formed so as not to press the blood vessels of the male genitalia and the lower frame is formed so as to press the urethras of the male genitalia.

4 Claims, 5 Drawing Sheets

(52) U.S. Cl.
CPC ............ *A61F 2/0031* (2013.01); *A61B 17/12* (2013.01); *A61B 17/122* (2013.01); *A61F 2220/0033* (2013.01); *A61F 2250/0009* (2013.01); *A61F 2250/0018* (2013.01)

(58) Field of Classification Search
CPC .............. A61B 17/132; A61B 17/1322; A61B 17/1325; A61B 17/1327
USPC .................. 128/885; 606/151, 157, 201, 203
See application file for complete search history.

(56) References Cited

U.S. PATENT DOCUMENTS

| | | | |
|---|---|---|---|
| 4,549,530 A | 10/1985 | Finney | |
| 4,592,355 A * | 6/1986 | Antebi | A61B 17/122 606/144 |
| 4,942,886 A * | 7/1990 | Timmons | A61B 17/132 128/885 |
| 5,160,339 A * | 11/1992 | Chen | A61B 17/0487 227/902 |
| 5,234,449 A * | 8/1993 | Bruker | A61B 17/122 227/902 |
| 5,571,125 A | 11/1996 | Chadwick | |
| 6,131,576 A | 10/2000 | Davis | |
| 6,234,174 B1 * | 5/2001 | Cheng | A61F 2/0054 128/885 |
| 6,289,895 B1 | 9/2001 | Cheng et al. | |
| 6,981,505 B2 * | 1/2006 | Krause | A61F 2/0054 128/885 |
| D767,761 S * | 9/2016 | Babb | D24/143 |
| 2004/0173219 A1 | 9/2004 | Bakane et al. | |
| 2008/0121241 A1 | 5/2008 | Dennis | |

FOREIGN PATENT DOCUMENTS

| | | |
|---|---|---|
| JP | 60-217954 A | 10/1985 |
| JP | 10-108874 A | 4/1998 |
| KR | 10-1310270 B1 | 9/2013 |
| KR | 20-2014-0001724 U | 3/2014 |
| KR | 10-2014-0104212 A | 8/2014 |

OTHER PUBLICATIONS

International Search Report for PCT/KR2016/006362 dated Feb. 14, 2017 from Korean Intellectual Property Office.
Office Action for related Japanese Patent Application No. 2018-560456.

* cited by examiner

URINARY INCONTINENCE PREVENTION CLIP FOR MEN

TECHNICAL FIELD

The present invention relates to a urinary incontinence prevention clip for men, and more specifically, to a urinary incontinence prevention clip for men configured to press the urethra of a male urinary incontinence patient to conveniently prevent urination along the urethra.

BACKGROUND ART

Urinary incontinence is a situation in which urination is performed against will, and means a case in which adjustment of a urethra is performed by power of a sphincter which surrounds a urethra, and urine is not filled in a bladder and flows against will when the power of the sphincter is insufficient.

Recently, since the average life expectancy has increased and thus the number of old people has increased, the incidence of urinary incontinence is increasing. Particularly, since male urinary incontinence occurs in over half of patients due to a side effect of prostate surgery, and when a person becomes over 50 years old, a sphincter becomes weaker with aging, the number of urinary incontinence patients is increasing.

Treatment of urinary incontinence includes a surgery to insert an apparatus configured to press the urethra in a body, and the like, but since the above is not perfect due to reoccurrence or the like, and there is a tendency to avoid the surgery, a urinary incontinence pad or urinary incontinence underwear is mostly used.

However, when the pad or the urinary incontinence underwear is used, the pad should be frequently changed, and since the pad is always wet and skin which comes into contact with the pad is weakened, an injury such as a case in which the skin is abraded, or the like, often occurs and a social phobia occurs due to the smell, and thus quality of life is degraded.

Particularly, in a severe case, the pad is not changed and then an outer garment can become wet.

To resolve these problems, in Japanese Laid Open Publicized Utility Model No. 55-070111, as a means for pressing the urethra, a structure in which upper and lower frames are connected by a hinge and a band and a hook for engaging the band are provided at each of both ends of the frame to pull and fix the band by engaging the band with the hook, is disclosed.

In Registered Utility Model Publication No. 20-474181 devised by the present inventor, a connection part capable of using an inherent elastic force of a synthetic resin frame instead of a hinge is provided, an engaging piece is formed at an end portion of the upper frame, and a plurality of locking protrusions configured to match the engaging piece are formed at an end portion of the lower frame. Accordingly, an elastic force in which the upper and lower frames are connected in a U-shape is used when the synthetic resin frame is integrally formed and a clip is separated. The above is a convenient integrated structure in which the engaging piece of the upper frame is pressed by the plurality of locking protrusions to couple the engaging piece to one of the first to fifth locking protrusions according to need.

However, according to a case in which the present inventor uses the clip manufactured by a method in the above-described Utility Model Publication, since elasticity of the U-shaped part decreases when the clip is frequently used, inserting and separating a penis is inconvenient. Further, the engaging piece and the locking protrusions of the upper and lower frames are laterally pushed and separated according to movement or exercise of the body and then all stored urine is urinated at once when the upper and lower frames are coupled and worn.

Accordingly, the development of an improved urinary incontinence clip which overcomes the above-described disadvantages is required.

DISCLOSURE

Technical Problem

The present invention is directed to providing a urinary incontinence prevention clip for men, which is devised to solve problems in a urinary incontinence prevention clip of Registered Utility Model Publication No. 20-474181 devised by the present inventor including a problem in which elasticity of a U-shaped connection part decreases and thus an opening becomes narrow when the clip is frequently used, and a problem in which coupling of upper and lower frames which has to press a urethra while being used is laterally pushed and separated, and which can be easily and conveniently worn by male patients having urinary incontinence and can prevent urination while being used.

Further, the present invention is directed to providing a urinary incontinence prevention clip for men configured not to press a vein and an artery of a penis to be capable of preventing poor circulation in the penis.

In addition, the present invention is directed to providing a urinary incontinence prevention clip for men configured to additionally press the urethra of the penis.

Technical Solution

A urinary incontinence prevention clip for men of the present invention includes a clip body including an upper frame located to correspond to an upper part of male genitalia, a lower frame located to correspond to a lower part of the male genitalia, and a connection part connected to one side of each of the upper frame and the lower frame to provide an elastic force in a direction in which the upper frame and the lower frame are spaced from each other; a cushion part provided on the inside of each of the upper frame and the lower frame; and locking parts formed at both ends of the clip body to be fastened with each other, wherein the upper frame is formed to not press a blood vessel of the male genitalia and the lower frame is formed to press the urethra of the male genitalia.

The connection part may further include a V-shaped bent portion provided at a center of the connection parts to provide an additional elastic force.

The locking parts may include an engaging piece formed at one of the upper frame and the lower frame, and a locking piece having a locking protrusion formed at the other frame to match the engaging piece.

The locking protrusion may have at least one protruding partition formed thereon, and one V-shaped groove configured to match the protruding partition may be formed in the engaging piece.

The locking protrusions may be formed at multiple stages.

Two protruding partitions may be installed on both end portions of the locking protrusion, and a protruding part may be formed on a front end portion of the engaging piece to be inserted between the two protruding partitions.

The cushion part may include a plurality of cushion parts having different thicknesses to be changed and used according to pressing strength for a user.

An arc-shaped first recessed portion may be formed at a center of the upper frame, and a first pressing protrusion may be formed at a center of the lower frame.

An arc-shaped second recessed portion may be formed in the cushion part provided on the upper frame, and a second pressing protrusion may be formed on the cushion part provided on the lower frame.

Advantageous Effects

A urinary incontinence prevention clip for men according to the present invention is configured to be wearable and detachable in a one-touch method, and is easy to be manufactured in an integrated structure.

Further, since upper and lower frames are not released even during strenuous exercise, the urinary incontinence prevention clip for men according to the present invention can relieve the anxiety of a user.

In addition, the urinary incontinence prevention clip for men according to the present invention can adjust a pressing force and thus can be worn by varying the pressing force according to a state of a urinary incontinence male patient.

In addition, since the urinary incontinence prevention clip for men according to the present invention can be anatomically configured to not press a vein and an artery of a penis, poor circulation in the penis can be prevented.

In addition, the urinary incontinence prevention clip for men according to the present invention additionally presses the urethra of the penis and thus is more efficient for urinary incontinence.

DESCRIPTION OF DRAWINGS

FIG. 4A illustrates a protruding partition provided at a center of a groove, and FIG. 4B illustrates two protruding partitions installed at both sides.

MODES OF THE INVENTION

Hereinafter, an embodiment of the present invention will be described in detail with reference to the accompanying drawings.

Figure 1:
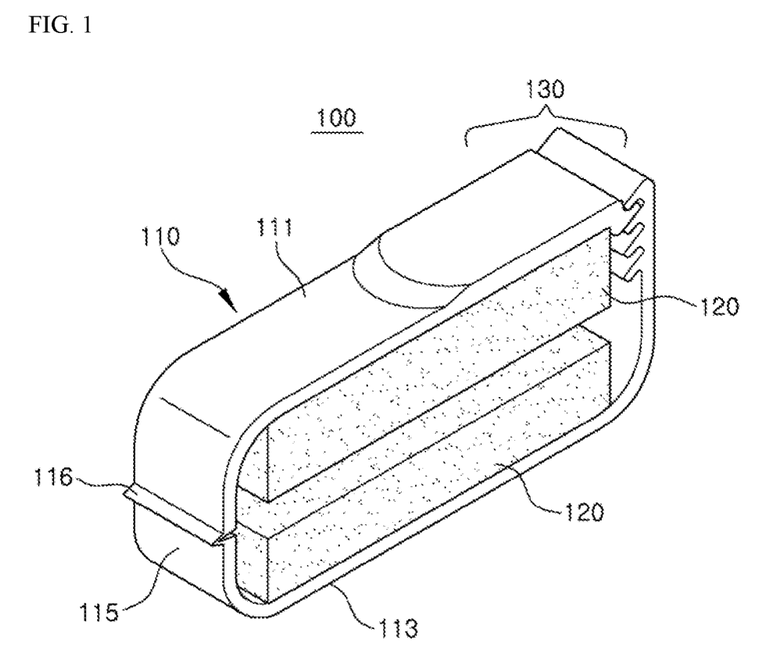
FIG. 1 is a perspective view illustrating a locked state of a urinary incontinence prevention clip for men according to the present invention.
Figure 2:
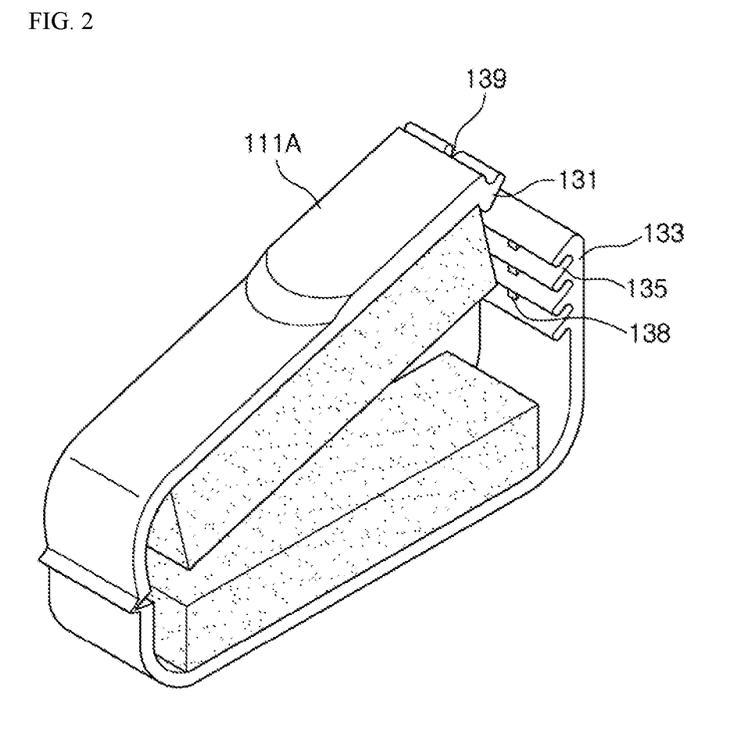
FIG. 2 is a view illustrating a state in which the urinary incontinence prevention clip for men shown in FIG. 1 is not locked.
Figure 3:
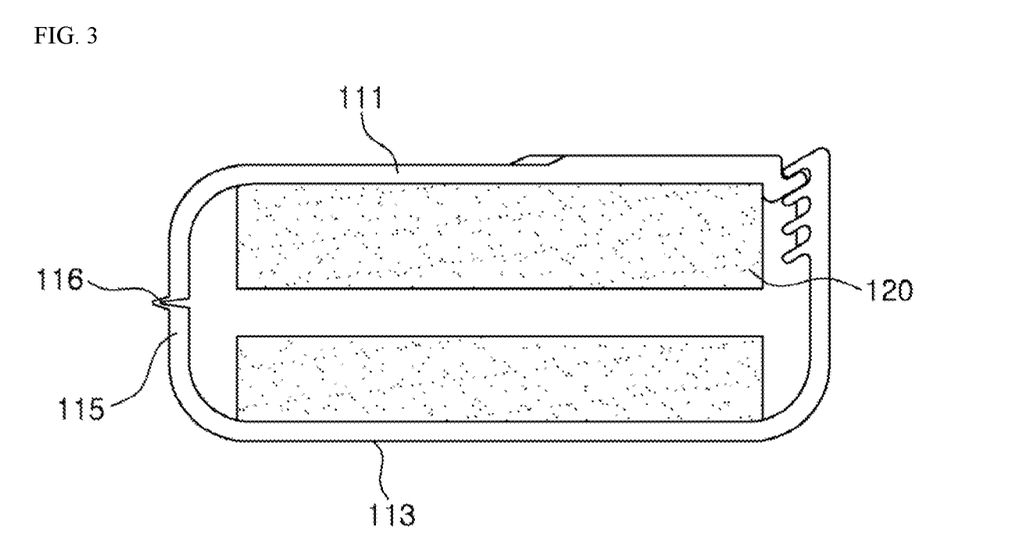
FIG. 3 is a side view illustrating the urinary incontinence prevention clip for men shown in FIG. 1.
Figure 4:
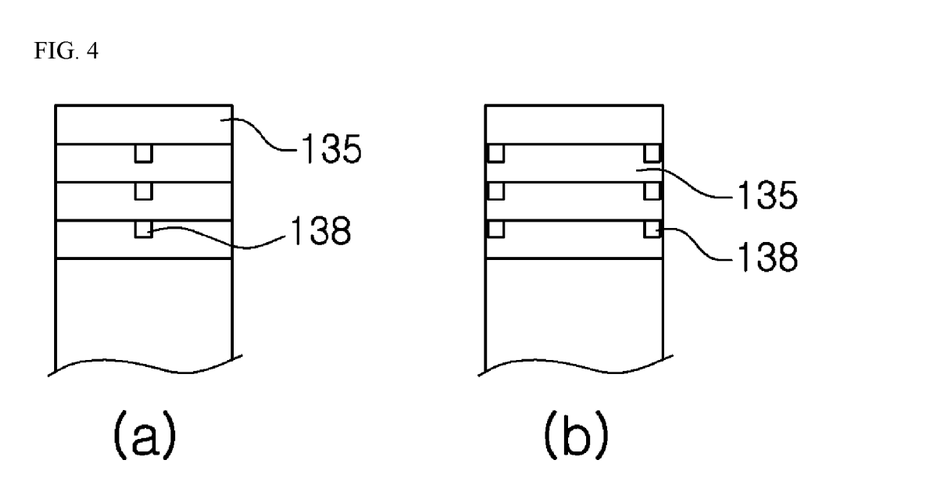
FIG. 4 is a view illustrating locking protrusions of two embodiments of the present invention.
Figure 5:
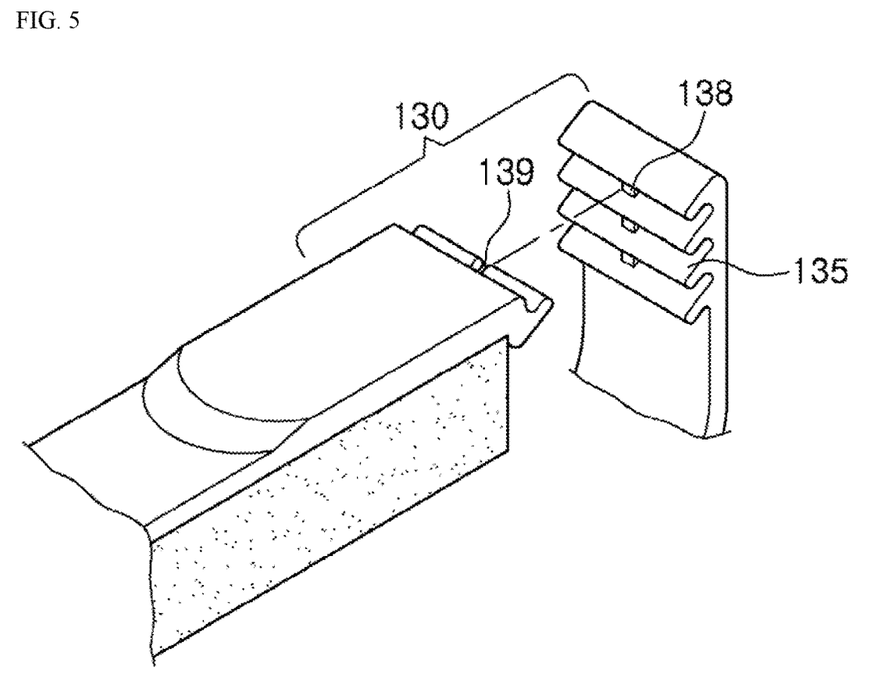
FIG. 5 is a perspective view of the embodiment in FIG. 4A.
Figure 6:
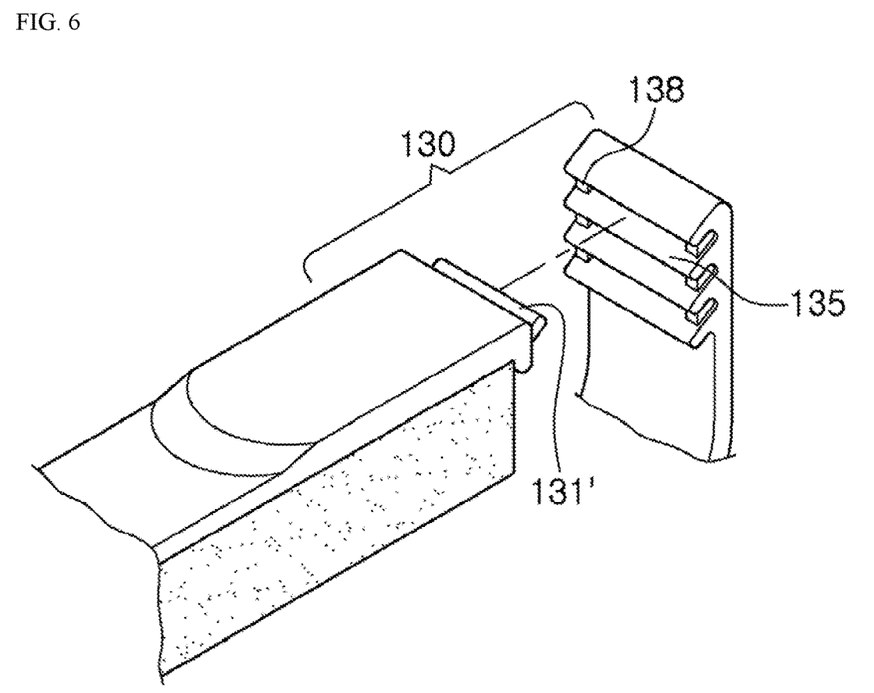
FIG. 6 is a perspective view of the embodiment in FIG. 4B.
Figure 7:
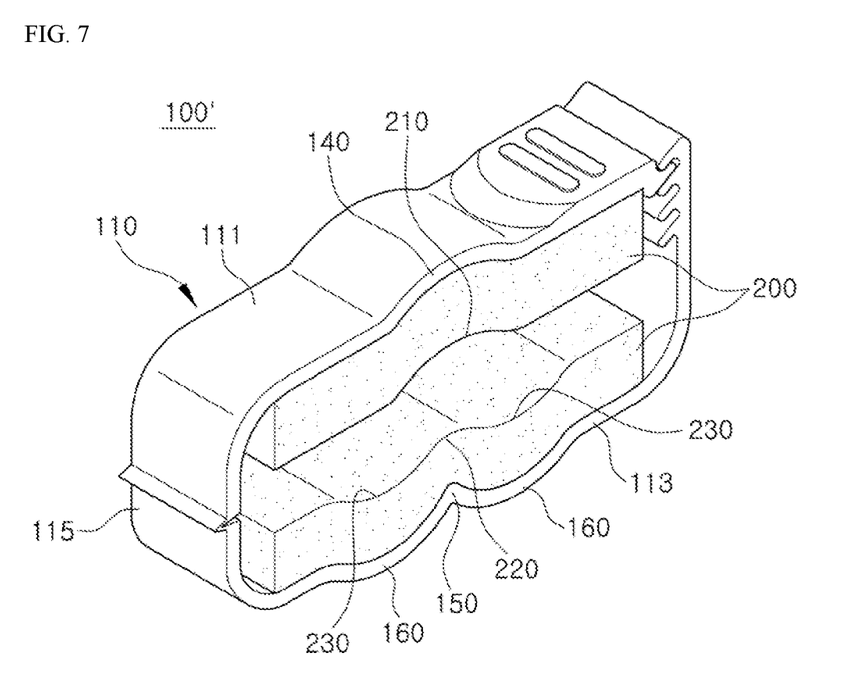
FIG. 7 is a perspective view illustrating a locked state of a urinary incontinence prevention clip for men according to another embodiment of the present invention.
Figure 8:
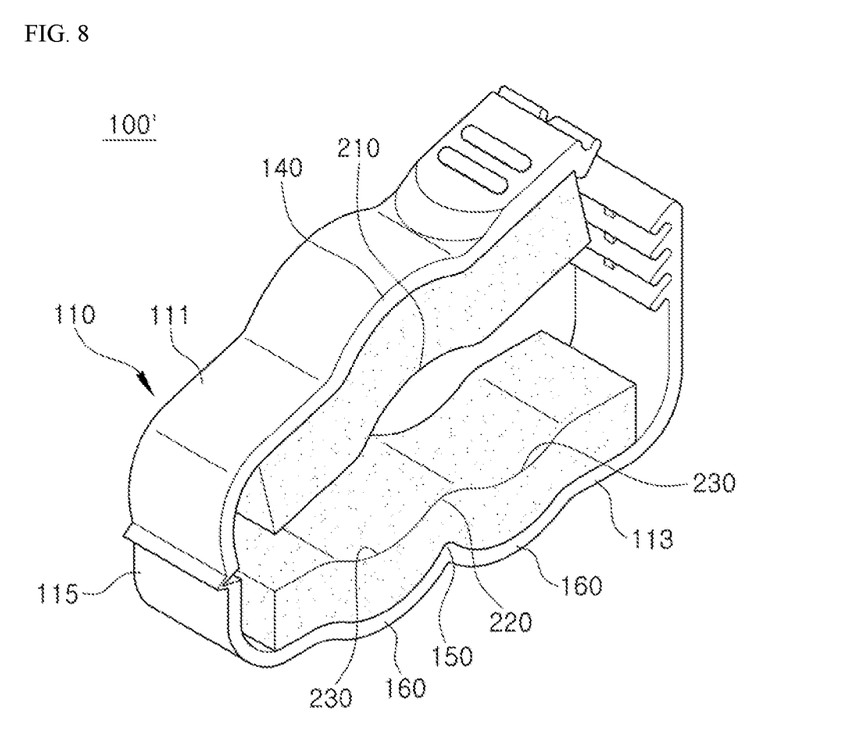
FIG. 8 is a view illustrating a state in which the urinary incontinence prevention clip for men shown in FIG. 7 is not locked.
Figure 9:
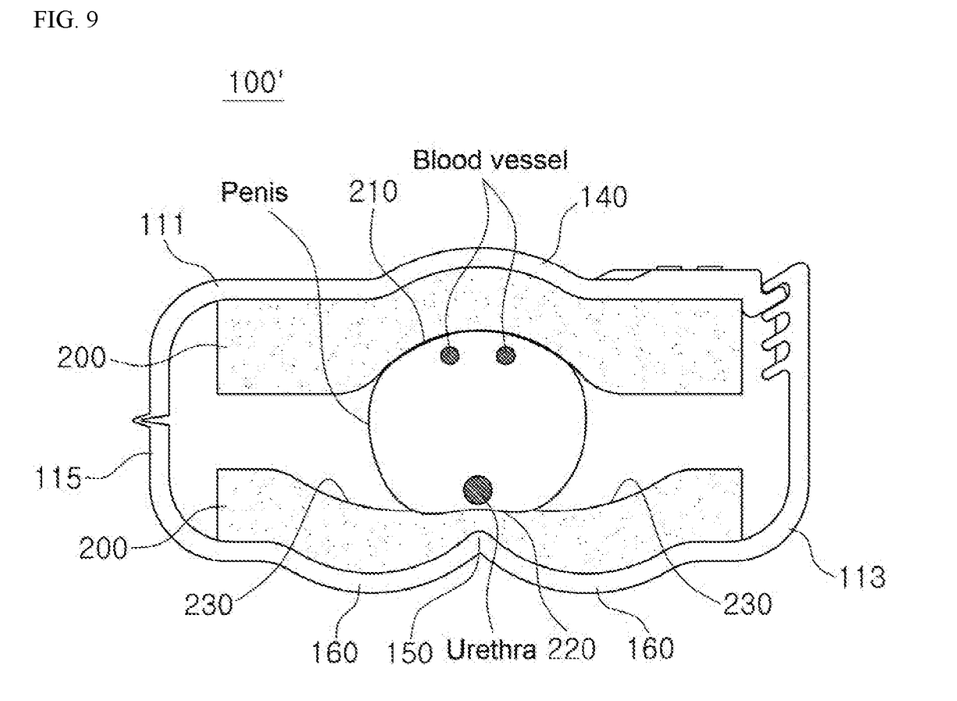
FIG. 9 is a view illustrating a state in which the urinary incontinence prevention clip for men shown in FIG. 7 is used.

FIG. 1 is a perspective view illustrating a locked state of a urinary incontinence prevention clip for men according to the present invention, FIG. 2 is a view illustrating a state in which the urinary incontinence prevention clip for men shown in FIG. 1 is not locked, FIG. 3 is a side view illustrating the urinary incontinence prevention clip for men shown in FIG. 1, FIG. 4 is a view illustrating locking protrusions of two embodiments of the present invention, FIG. 4A illustrates a protruding partition provided at a center of a groove, and FIG. 4B illustrates two protruding partitions installed at both sides, FIG. 5 is a perspective view of the embodiment in FIG. 4A, FIG. 6 is a perspective view of the embodiment in FIG. 4B, FIG. 7 is a perspective view illustrating a locked state of a urinary incontinence prevention clip for men according to another embodiment of the present invention, FIG. 8 is a view illustrating a state in which the urinary incontinence prevention clip for men shown in FIG. 7 is not locked, and FIG. 9 is a view illustrating a state in which the urinary incontinence prevention clip for men shown in FIG. 7 is used.

As shown in FIG. 1, a urinary incontinence prevention clip for men 100 includes an integrally formed clip body 110 located to correspond to an upper part and a lower part, a cushion part 120 fixed to the inside of the clip body 110 and configured to come into contact with male genitalia, locking parts 130 formed at both ends of the clip body 110 and fastened with each other to be locked or unlocked.

Hereinafter, the above-described urinary incontinence prevention clip for men will be specifically described.

The clip body 110 includes an upper frame 111 and a lower frame 113 located to face each other, and a connection part 115 to which one sides of the upper frame 111 and the lower frame 113 are connected to each other, and the upper frame 111, the lower frame 113, and the connection part 115 are formed in one body as an integrated structure.

Here, the connection part 115 provides an elastic force so that the upper frame 111 and the lower frame 113 are spaced apart from each other. Accordingly, an elastic restoring force is generated when the other side of each of the upper frame 111 and the lower frame 113 is locked by the locking parts 130 in a state in which the upper frame 111 and the lower frame 113 come into contact with each other, and the upper frame 111 and the lower frame 113 are spaced apart from each other in directions away from each other when the locking parts 130 are unlocked by an elastic restoring force provided from the connection part 115.

A V-shaped bent portion 116 is provided at a center of the connection part 115 to provide an additional elastic force. Since a broad side is disposed at an inner side in the V-shape and thus a folding force and the elastic force of each of the upper and lower frames 111 and 113 are reinforced, the elastic force does not lose elasticity for opening and folding the upper and lower frames even when the urinary incontinence prevention clip for men is used for a long time.

Further, each of the upper frame 111 and the lower frame 113 has rigidity so as not to be elastically deformed in a locked state. Accordingly, although described below, the cushion parts 120 may maintain rigidity capable of pressing the male genitalia from the top and bottom even when the male genitalia (a penis) is located between the cushion parts 120 and locked by the locking parts 130.

Meanwhile, a locking part 130 is formed at the other side of each of the upper frame 111 and the lower frame 113.

As shown in FIG. 2, an engaging piece 131 is formed at the other end portion of the upper frame 111, a locking piece 133 is formed at the other end portion of the lower frame 113, and the engaging piece 131 is engaged with the locking piece 133 to lock the upper frame 111 and the lower frame 113.

Here, the locking piece 133 is upwardly bent toward the engaging piece 131, and has locking protrusions 135 formed at multiple stages. Gaps between the locking protrusions 135 maintain an interval greater than a thickness of the engaging piece 131, and the engaging piece 131 is matched into the locking protrusion 135 to be locked when the upper frame 111 and the lower frame 113 are locked.

Accordingly, as shown in FIGS. 2 and 3, the elastic restoring force of the connection part 115 is large when the engaging piece 131 is matched with a lower locking protrusion 135 among the locking protrusions 135, and the elastic restoring force of the connection part 115 is weak when the engaging piece 131 is matched with an upper locking protrusion 135 among the locking protrusions 135. Accordingly, a urinary incontinence male patient may use the locking parts 130 and lock the upper frame 111 and the lower frame 113 to adjust a pressing force which presses a penis 1. Further, to be unlocked from a locked state, when the locking piece 133 is pushed to the outside, the engaging piece 131 is separated from the locking protrusion 135 and unlocked, and thus the upper frame 111 and the lower frame 113 are spaced apart from each other by the elastic restoring force of the connection part 115.

As shown in FIGS. 4 to 6, at least one protruding partition 138 is formed between grooves between the locking protrusions of the lower frame and a V-shaped groove 139 configured to match the protruding partition 138 is provided in a front end of the engaging piece of the upper frame so that the upper and lower frames are not laterally pushed and thus coupling between the engaging piece of the upper frame and the locking protrusion of the lower frame is not released during use (see FIGS. 1 to 5). In a modified embodiment, two or more protruding partitions 138 may be formed between the grooves between the locking protrusions of the lower frame, and a protruding part 131' which may be matched between the protruding partitions 138 may be provided (see FIG. 6).

As shown above, the locking protrusions 135 are formed at multiple stages. Accordingly, since the pressing force may be adjusted, the urinary incontinence prevention clip for men may be worn by changing the pressing force according to a state of the urinary incontinence male patient.

Meanwhile, the cushion part 120 is located on the inside of each of the upper frame 111 and the lower frame 113. The cushion part 120 may be made of one of urethane, silicone, and latex, and is preferable to be formed of silicone foam which is a material similar to a human body. Further, a thickness of the cushion part 120 may be selected by a user.

In addition, when pressing strength of the clip cannot be adjusted by the multiple stages of the above-described locking protrusions 135, the cushion part 120 may be changed and used. For example, the cushion part 120 having a great thickness may be used when a strong pressure is necessary, and the cushion part 120 having a small thickness may be used when a weak pressure is necessary.

Further, as shown in FIG. 1, protrusions 111A formed on an outer surface of the upper frame 111 are sliding prevention members formed so that fingers do not slide when the upper frame 111 is pushed toward the lower frame 113. Here, although not shown in the drawings, the sliding prevention members may be formed on an outer surface of the lower frame 113 in addition to the outer surface of the upper frame 111.

Since a method of using the present invention is disclosed in Registered Utility Model Publication No. 20-474181 devised by the present inventor, Registered Utility Model Publication No. 20-474181 should be referenced if desired, and detailed descriptions will be omitted.

Hereinafter, in a description of a urinary incontinence prevention clip for men according to another embodiment of the present invention, the same reference numerals are used for components having the same functions as those of the above-described components, and detailed descriptions will be omitted.

As shown in FIGS. 7 to 9, a urinary incontinence clip for men 100' according to another embodiment of the present invention includes: a clip body 110 including an upper frame 111 located to correspond to an upper part of male genitalia, a lower frame 113 located to correspond to a lower part of the male genitalia, and a connection part 115 connected to one side of each of the upper frame 111 and the lower frame 113 to provide an elastic force in a direction in which the upper frame 111 and the lower frame 113 are spaced from each other; and a cushion part 120 provided on the inside of each of the upper frame 111 and the lower frame 113.

An arc-shaped first recessed portion 140 is formed at a center of the upper frame 111, and a first pressing protrusion 150 is formed to protrude at a center of the lower frame.

An arc-shaped second recessed portion 210 is formed in the cushion part 200 provided on the upper frame 111 and a second pressing protrusion 220 is formed on the cushion part 200 provided on the lower frame 113.

Accordingly, as shown in FIG. 9, since the first and second recessed portions 140 and 210 may be configured to not press a vein and an artery of the penis, poor circulation in the penis may be prevented.

Further, the first and second pressing protrusions 150 and 220 additionally press the urethra of the penis to prevent urinary incontinence.

Meanwhile, since two first elastic members 160 each formed in an arc shape are formed at both sides of the first pressing protrusion 150, and two elastic members 230 each formed in an arc shape are formed at both sides of the second pressing protrusion 220, the first and second pressing protrusions 150 and 220 press the urethra due to an elastic force of each of the first and second elastic members 160 and 230.

As described above, although preferable embodiments of the present invention have been described in detail, the technical scope of the present invention is not limited to the above-described embodiments and should be construed according the scope of the claims. In this case, those skilled in the art will appreciate many changes and modifications are possible without departing from the scope of the present invention.

The invention claimed is:

1. An urinary incontinence prevention clip for men comprising:
   a clip body including an upper frame located to correspond to an upper part of male genitalia, a lower frame located to correspond to a lower part of the male genitalia, and a connection part connected to one side of each of the upper frame and the lower frame to provide an elastic force in a direction in which the upper frame and the lower frame are spaced from each other;
   a cushion part provided on the inside of each of the upper frame and the lower frame; and
   locking parts formed at both ends of the clip body to be fastened with each other, wherein the upper frame includes an arc-shaped first recessed portion formed at a center of an inner side of the upper frame for not pressing a blood vessel of the male genitalia, wherein the lower frame includes a first pressing protrusion and a pair of first elastic members, the first pressing protrusion being formed at a center of an inner side of the lower frame to press an urethra of the male genitalia, and the first elastic members being formed in an arch shape at left and right sides of the first pressing protrusion, wherein the pair of first elastic members form an outer surface of the lower frame, wherein an recessed portion is formed at an outer portion of the first pressing protrusion, wherein the connection part includes a V-shaped bent portion provided at a center of the connection part to provide an additional elastic force, thereby providing a reinforced elastic force, wherein the locking parts include an engaging piece formed at one end of the upper frame and a locking piece formed at one end of the lower frame, the locking piece having a plurality of locking protrusions and a plurality of protruding partitions, the locking protrusions protruding in a horizontal direction at intervals, the protruding partitions being formed between the locking protrusions, wherein the engaging piece is configured to be inserted between the locking protrusions and includes a groove configured to match one of the protruding partitions in order to prevent left and right movement of the engaging piece between the locking protrusions.

2. The urinary incontinence prevention clip for men of claim 1, wherein:

the plurality of protruding partitions include two protruding partitions installed on both end portions of each of the locking protrusions; and a protruding part is formed on a front end portion of the engaging piece to be inserted between the two protruding partitions.

3. The urinary incontinence prevention clip for men of claim 1, wherein the cushion part includes a plurality of cushion parts having different thicknesses to be changed and used according to pressing strength for a user.

4. The urinary incontinence prevention clip for men of claim 1, wherein the cushion part provided on the upper frame includes an arc-shaped second recessed portion formed at a center of an inner side thereof, and the cushion part provided on the lower frame includes a second pressing protrusion formed on a center of an inner side thereof and a pair of second elastic members formed in an arch shape at left and right sides of the second pressing protrusion.

\* \* \* \* \*